United States Patent [19]

Piskorski

[11] Patent Number: 5,794,613

[45] Date of Patent: Aug. 18, 1998

[54] MULTIPLE-DOSE DISPENSER FOR DRY POWDER INHALERS

[75] Inventor: Walter Piskorski, Londonderry, N.H.

[73] Assignee: Sepracor, Inc., Marlborough, Mass.

[21] Appl. No.: 780,801

[22] Filed: Jan. 9, 1997

[51] Int. Cl.⁶ ............................................. A61M 15/00
[52] U.S. Cl. ................. 128/203.12; 128/203; 128/12; 128/21
[58] Field of Search .................. 222/83, 83.5, 86, 222/144, 325; 206/532, 538, 540, 438; 220/4.24, 504, 507; 128/203.15, 203.21, 203.12, 200.21

[56] References Cited

U.S. PATENT DOCUMENTS

| | | | |
|---|---|---|---|
| 4,307,734 | 12/1981 | Blankenshipq | 128/203.15 |
| 5,239,993 | 8/1993 | Evans. | |
| 5,301,666 | 4/1994 | Lerk et al. | 128/203.15 |
| 5,337,740 | 8/1994 | Armstrong et al. | |
| 5,388,572 | 2/1995 | Mulhauser et al. | |
| 5,388,573 | 2/1995 | Mulhauser et al. | 128/203.15 |
| 5,492,112 | 2/1996 | Mecikalski et al. | 128/203.15 |
| 5,529,059 | 6/1996 | Armsrong et al. | 128/203.12 |

FOREIGN PATENT DOCUMENTS

| | | |
|---|---|---|
| 2178965 | 2/1987 | United Kingdom. |
| 2264237 | 8/1993 | United Kingdom. |
| 2274273 | 7/1994 | United Kingdom. |
| WO 93/00123 | 1/1993 | WIPO. |
| WO 94/06498 | 3/1994 | WIPO. |
| WO 94/08552 | 4/1994 | WIPO. |
| WO 94/12230 | 6/1994 | WIPO. |
| WO 94/14491 | 7/1994 | WIPO. |
| WO 94/20164 | 9/1994 | WIPO. |

*Primary Examiner*—Vincent Millin
*Assistant Examiner*—Robert N. Wieland
*Attorney, Agent, or Firm*—Heslin & Rothenberg, P.C.; Candice J. Clement

[57] ABSTRACT

A multiple-dose dispenser for use with dry powder inhalers is disclosed. The dispenser has a two-piece construction and includes a plurality of individual, hermetically sealed chambers for retaining unit doses of a dry powder for inhalation. Also disclosed is a method for producing the multiple-dose dispenser.

12 Claims, 3 Drawing Sheets

5,794,613

MULTIPLE-DOSE DISPENSER FOR DRY POWDER INHALERS

FIELD OF THE INVENTION

This invention relates generally to dry powder inhalation systems, and more specifically to multiple-dose dispensers for use with dry powder inhalers.

BACKGROUND OF THE INVENTION

Inhalation of therapeutic agents for treatment of certain respiratory disorders such as, e.g., bronchial asthma, is a well-known treatment modality. Therapeutic inhalation regimens typically involve inhalation of a desired therapeutic agent as a finely divided solid such as a dry powder or an aerosolized solution or suspension (delivered by way of a nebulizer or metered dose inhaler). Although numerous systems have been developed for inhalation with each of these dosage forms, dry powder inhalation has recently become more attractive as a result of certain disadvantages of aerosolized solutions or suspensions.

First, metered dose inhalers typically include halogenated hydrocarbons, compounds that are known to be environmentally damaging. Second, metered dose inhalers often require adept manipulation on the part of the user to insure complete and accurate dosing. Careful coordination between the release of the aerosolized dose from the inhaler and inhalation of the dose by the user is required. This task often proves difficult for many patients and as a result, quite frequently leads to patient frustration and non-compliance. Third, it is extremely difficult to monitor the number of doses remaining in the aerosol canister. Fourth, the drug is dissolved or suspended in a liquid propellant, which results in the unwanted introduction of foreign chemical substances into the body. Each of these disadvantages can be avoided by the use of dry powder inhalation dosage forms.

Several different types of dispensers are available for use with dry powder inhalation systems. These include bulk powder dispensers, single dose dispensers and multiple-dose dispensers. Bulk powder dispensers hold enough bulk powder for a plurality of doses and are typically used with an inhaler having a shuttle or rotary mechanism that transfers a metered dose from the bulk powder reserve into an inhalation chamber in the inhaler. Reference is made to PCT Patent WO 93/00123, published Jan. 7, 1993 and to U.S. Pat. No. 5,239,993, issued Aug. 31, 1993 to Evans. Bulk powder inhalation systems have several disadvantages. For example, once the system has been activated to dispense the first dose, the bulk powder is no longer sealed from the external environment, and also, it is very difficult for the user to monitor the number of doses remaining in the bulk powder dispenser.

An example of a single dose dispenser is provided in PCT Patent WO/94/06498, published Mar. 31, 1994. This patent discloses a dry powder inhaler system adapted to engage a single dose gelatin capsule. Although a single dose dispenser, such as a gelatin capsule, has the advantage of maintaining the integrity of the dry powder until the time of dispensing, this method requires a much higher level of user involvement. Each time a dosage is to be dispensed, the user must insert a new capsule into the device and then, following dispensing, remove the empty capsule shell. This action often requires that the device be dismantled. In an acute situation, such as a bronchial asthma attack, or for those with impaired hand movement, such as an elderly or disabled patient, this procedure can prove to be overly difficult and cumbersome.

The third type of dry powder dispensers, multiple-dose dispensers, have a number of unit doses secured in individual chambers. An example is described in UK Patent Application GB 2,274,273 A, published Jul. 20, 1994. This reference teaches a medicament pack that comprises an elongate base strip having a plurality of recesses spaced along its length and a lid sheet hermetically but peelably sealed thereto, thereby defining a number of cavities for inhalable dry powdered medicaments. A second example of a multiple-dose dispenser is disclosed in U.S. Pat. 5,388,572 issued Feb. 14, 1995 to Mulhauser et al. This patent discloses a mesh disc impregnated with a series of spaced, medicament doses about the disc periphery. A major drawback to this dispenser is that the doses are not individually hermetically sealed.

Although dry powder systems enjoy a number of theoretical advantages over metered dose inhaler systems, they have not reached their full potential due to certain shortcomings of known dry powder systems. Thus, there exists a need for a multiple-dose dispenser for use with dry powder inhalers wherein each of the individual powder chambers is individually, hermetically sealed. The dispenser should also include a means for indicating to the user how many doses remain in the dispenser, as well as a means for clearly indicating when all of the doses have been administered. The dispenser should have the capability of being efficiently and easily filled with accurate, small volume dry powder dosages. The individual hermetically sealed chambers should be sized such that there is sufficient head space and that the dry powder is not compacted within the chambers.

SUMMARY OF THE INVENTION

The present invention provides a multiple-dose dispenser for use with dry powder inhalers. The dispenser includes a plurality of individual hermetically sealed chambers, each retaining a unit dose of a desired dry powder for inhalation. Thus, the integrity of each dry powder dose is maintained until the seal on a particular chamber is broken.

The multiple-dose dispenser is comprised of a first portion and a second portion, each having a plurality of cavities extending therethrough. One end (the same end) of each of the cavities in both the first portion and in the second portion is sealed with a conventional sealing means and one cavity in the second portion is so sealed on each end. The first portion and the second portion are bonded together, preferably by ultrasonic welding, wherein the open ends of the cavities in the two portions are in alignment, forming a number of individual hermetically sealed chambers. In practical realization, each of the chambers contains a unit dose of a desired dry powder.

The cavity in the second portion which is sealed on each end provides a means to assist the user in inserting the dispenser into the proper dispensing position in a dry powder inhaler and to prevent inadvertent "double dosing" during the initial dispensing process.

In one embodiment, the dispenser is disc-shaped and the cavities are circumferentially located. Preferably, the volume of each cavity in the second portion is equal to the volume of powder required for one dose. Therefore, the full volume of powder is retained in the second portion and the corresponding cavity in the first portion remains empty, providing head space and preventing compaction of the powder. Preferably, the chambers are cylindrically or conically shaped, allowing the dry powder to freely flow from a chamber when the seal is broken during the dispensing process.

Another embodiment of the dispenser includes means, such as reference numerals or the like, for indicating to the user how many doses remain in the dispenser and for clearly indicating to the user that the dispenser is empty. Thus, the user is able to efficiently monitor replacement of the dispenser, thereby improving patient compliance and ensuring that doses will be available when needed.

Another embodiment of the multiple dose dispenser of the present invention includes a drive means for functionally indexing the individual sealed chambers into the proper dispensing position when the dispenser is inserted into a dry powder inhaler. Preferably, the drive means is a set of ratchet teeth located on the outer periphery of the dispenser, on either the first or the second portion. Each of the ratchet teeth is spaced to correspond to one of the sealed chambers and therefore, as the dispenser is rotated, the next sequential dose is properly positioned for dispensing. As a means for unambiguously informing the user that the dispenser is empty, i.e., that no doses remain, a chamber adjacent to the cavity sealed on each end (the empty chamber) does not have a corresponding ratchet tooth and consequently, after this dose has been dispensed, the dispenser can not be rotated to the next position, that of the blocked cavity.

Thus, an aspect of the present invention is a method for producing a multiple-dose dispenser for use with a dry powder inhaler comprising the steps of:

providing a first portion and a second portion, each portion having a plurality of cavities extending therethrough;

sealing one end of each cavity;

sealing a second end of one of the cavities in the second portion;

filling each of the open cavities in the second portion with a unit dose of a dry powder;

bonding the first portion to the second portion such that the open end of each of the cavities in the second portion is aligned with an open end of a cavity in the first portion forming a plurality of sealed chambers.

As the volume of each of the cavities in the second portion is equal to the volume of one dose, in another aspect of the invention, the step of filling each of the open cavities comprises overfilling each of the cavities with an excess volume of a bulk powder and removing the excess powder to form a level powder surface in each of the cavities.

In yet another aspect of the invention, the step of bonding the first portion to the second portion comprises ultrasonic welding, wherein each of the sealed chambers is hermetically sealed.

BRIEF DESCRIPTION OF THE DRAWINGS

Numerous other advantages and features of the present invention will become readily apparent from the following detailed description of the preferred embodiment, the appended claims and the accompanying drawings wherein:

DETAILED DESCRIPTION OF THE PREFERRED EMBODIMENTS

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated.

Figure 1:
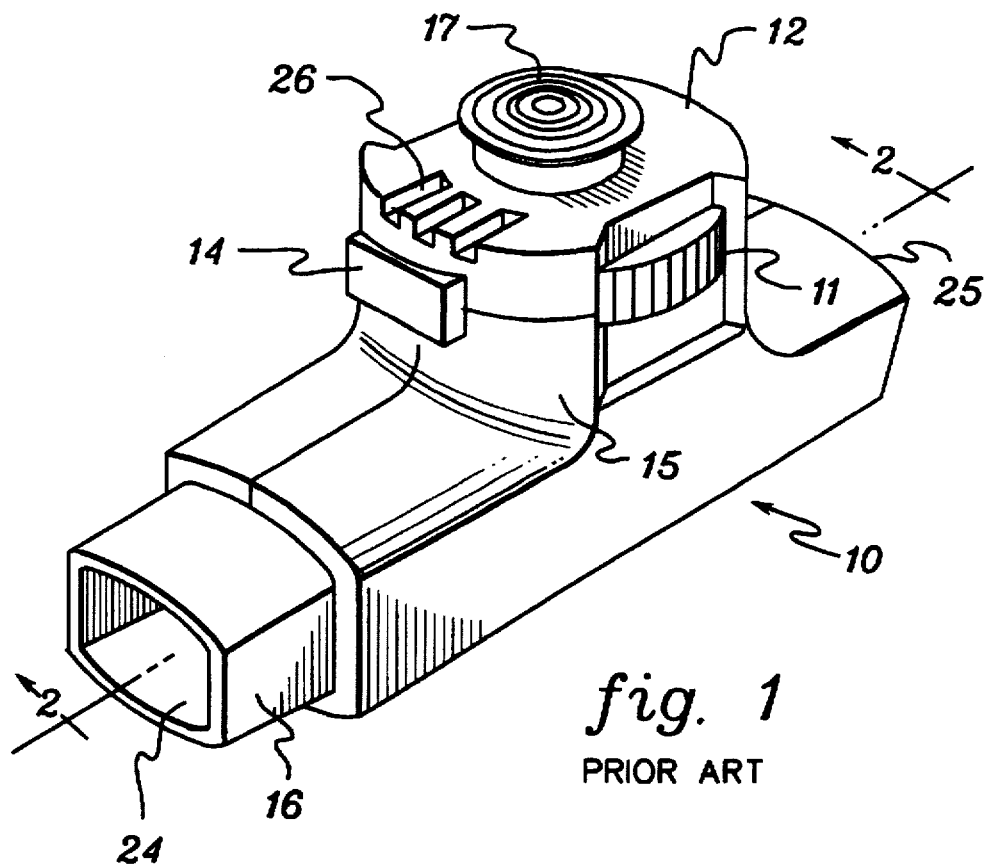
FIG. 1 is a perspective view of a prior art dry powder inhaler.
Figure 2:
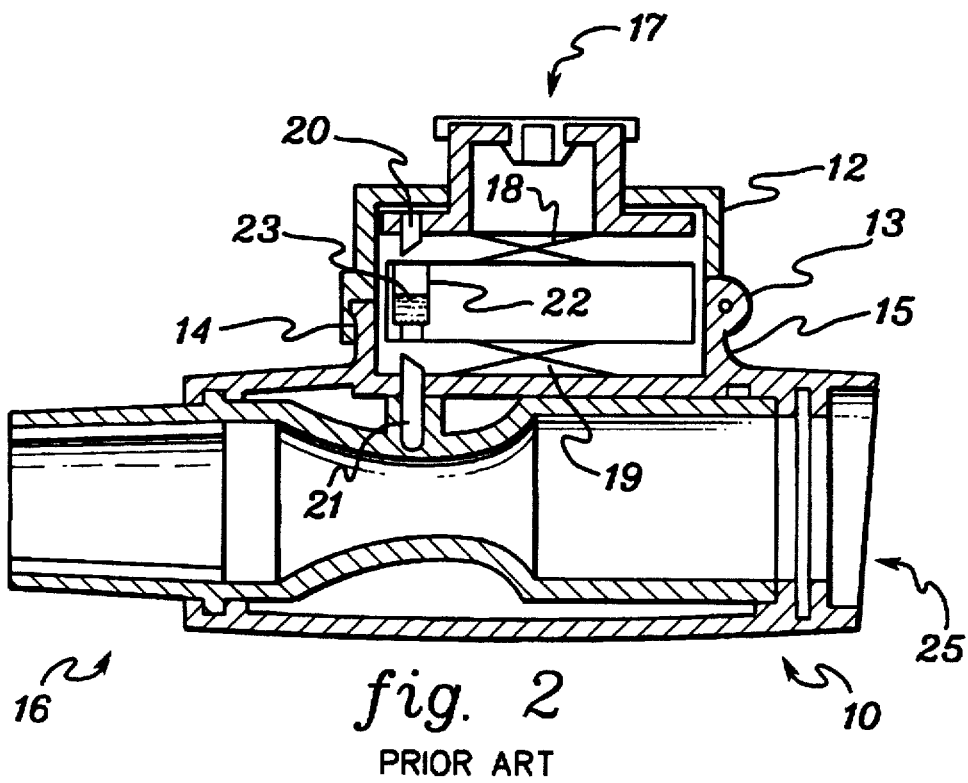
FIG. 2 is a cross-sectional view of the dry powder inhaler of FIG. 1, taken along line 2—2.

Referring now to the drawings, FIGS. 1 and 2 depict dry powder inhaler 10 having a multiple-dose powder dispenser disk 11 mounted therein. The inhaler device is described in detail in U.S. Pat. No. 5,337,740 (to Armstrong et al), the entire contents of which is incorporated herein by reference. To operate inhaler 10, cover 12, which rotates on hinge 13 when latch 14 is released, is opened and disk 11 is functionally inserted into receptacle 15 and cover 12 replaced. Mouthpiece 16 is inserted into the mouth of the user and movable section 17 is depressed. This action causes springs 18 and 19 to be compressed, which in turn causes hollow piercers 20 and 21 to pierce seals (not shown) on disk 11 which cover the ends of powder filled cavity 22, thus creating an air passage through cavity 22. The air passage is blocked only by dry powder 23, because the tab of pierced cavity seal (not shown) is held against the side of cavity 22 by hollow piercer 21. Movable section 17 is held in a depressed position until the user has inhaled, so that piercers 20 and 21 remain in contact with cavity 22. The user inhales air into air passageway 24 through air intake end 25 and vents 26. The passage of air through vents 26, hollow piercer 20, cavity 22, hollow piercer 21, air intake end 25 and air passageway 24, virtually purges powder 23 from cavity 22, carrying it along with the user's inspired air into the lungs.

Referring now to FIGS. 4 through 7, there is shown a multiple dose powder dispenser 30 in accordance with the principles of the present invention. Dispenser 30 is suitable for use with typical dry powder inhalers known in the art. Dispenser 30 is comprised of a first portion 31 and a second portion 32, each portion having a plurality of cavities 33, 33' extending therethrough. While the invention is not intended to be limited by the shape of dispenser 30, first portion 31 and second portion 32 are preferably disc-shaped, wherein the plurality of cavities 33, 33' is circumferentially placed. First portion 31 and second portion 32 are preferably formed of high impact polystyrene, although other materials known in the art may also be used. Examples include, conventional molded plastics, such as polypropylene, polyethylene, acetal, ABS, injection molded thermoplastics and the like.

Dispenser 30 may be of any given diameter and may contain different numbers of cavities, depending on the requirements of the particular drug to be used. A preferred multiple-dose dispenser is about 1.9 to 3.2 cm in diameter and about 0.6 to 0.8 cm deep. While first portion 31 and second portion 32 may be substantially equal in diameter and thickness, they need not be. Indeed, one of the advantages of the two-piece construction according to the invention is that an asymmetric dispenser may be readily fabricated. One or the other of the portions might be somewhat larger in diameter, for example, whereby the asymmetry will assist the user in recognizing the proper "right-side-up" orientation when dispenser 30 is subsequently inserted into a dry powder inhaler. A minor modification of dispenser 30, such as a shoulder, can be used such that insertion in an improper orientation makes the unit mechanically nonfunctional. Similarly, either portion may include an arrow or other indicator to assist in proper functional alignment of dispenser 30 with inhaler 10.

Each of the cavities 33, 33' in first portion 31 and in second portion 32 is sealed on one end (the same end for each cavity) by a conventional pierceable seal such as, e.g., a plastic film, a metal film, such as aluminum foil or a metalized laminate. Sealing one end of cavities 33' in second portion 32 thus allows cavities 33' to retain a volume of dry powder. In a preferred embodiment of the invention, one of the cavities 33' in second portion 32 may be sealed or otherwise blocked on each end, thus completely blocking the cavity and preventing the subsequent filling of the cavity with dry powder.

Figure 4:
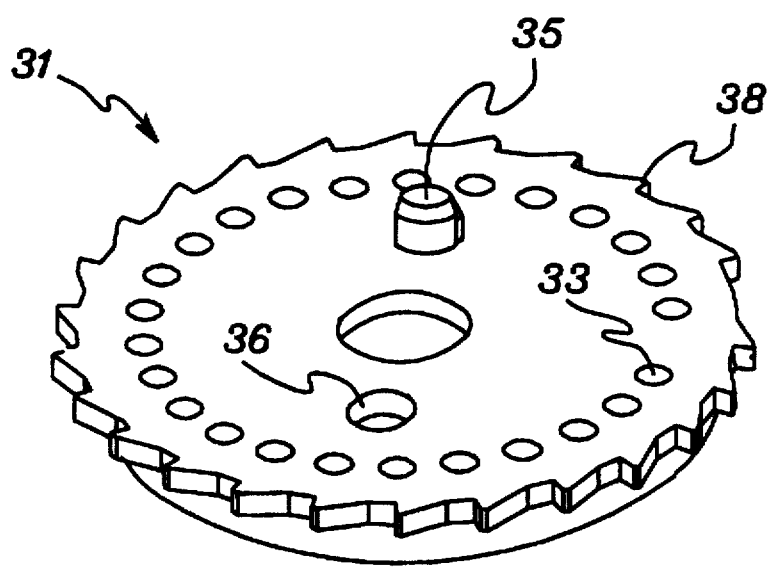
Figure 5:
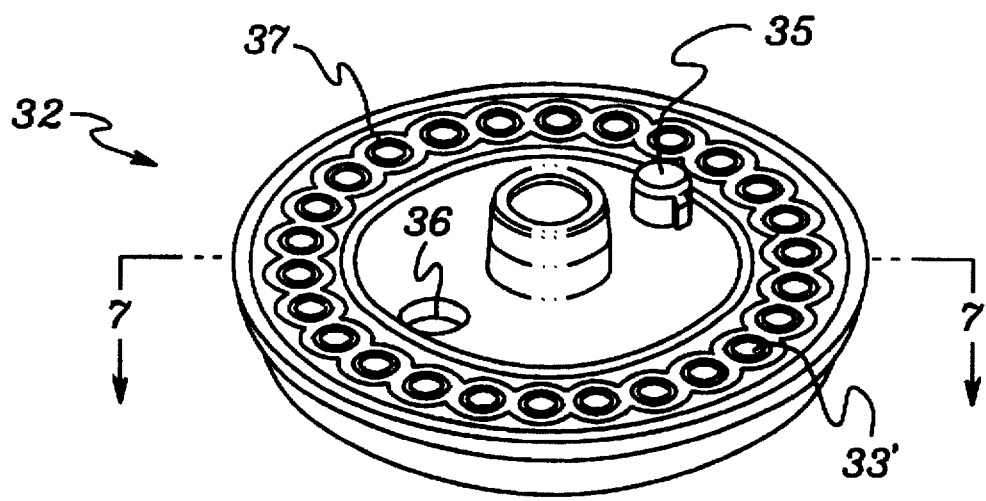
FIGS. 5 and 6 are perspective views of one embodiment of the second portion of the multiple-dose dispenser of the present invention.
Figure 6:
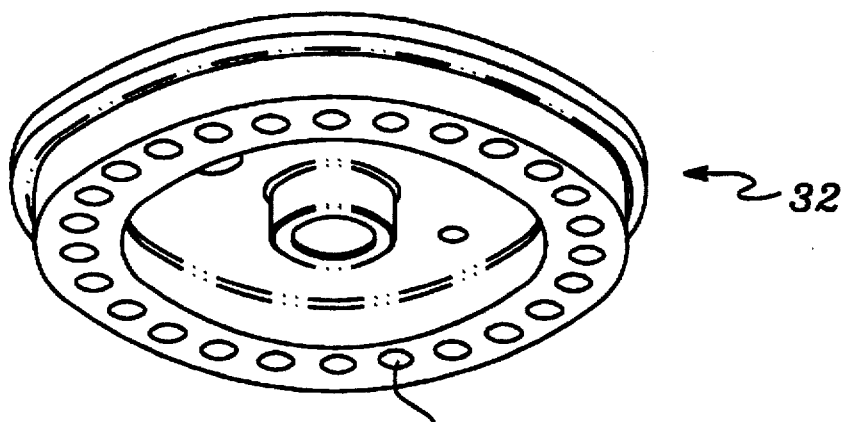
Figure 7:
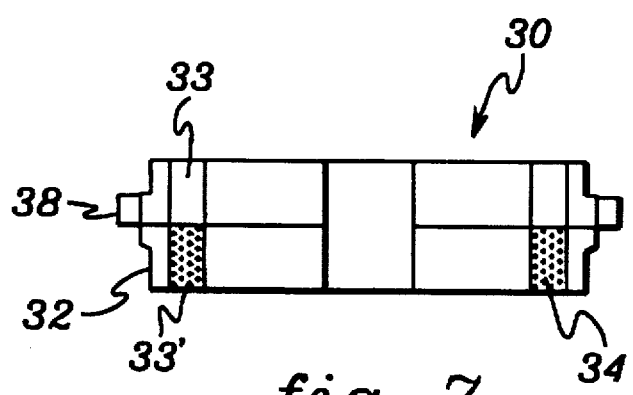
FIG. 7 is a cross-sectional view, taken along lines 7—7 of FIGS. 3 and 5, of the multiple dose dispenser of the present invention, following bonding of the first portion to the second portion.

Preferably, the volume of each cavity 33' in second portion 32, i.e., from the seal to the remaining open end, will be the volume required to retain one unit dose of a particular dry powdered drug 34 to be used. This facilitates the filling of dispenser 30 with unit doses of a particular drug powder 34 in that a bulk volume of the powder can be dropped into the powder chambers and the excess scraped away, leveling the powder surface and leaving an accurate, non-compacted volume of drug powder 34 in each chamber, as shown in FIG. 4. Thus, the typically small volume drug powder dosages are assured without the need for the intricate powder handling equipment generally necessary to accurately meter these small volumes. Following the bonding of first portion 31 to second portion 32, the depth of the cavities 33 in first portion 31 provides "head-space" to the sealed chambers, further preventing compaction of the drug powder.

As indicated, the two portions 31, 32 of dispenser 30 are bonded together, thus forming a single, integrated unit 30. The two portions 31, 32 are bonded together after the cavities 33' in second portion 32 have been filled. First portion 31 is positioned over second portion 32, having the open ends of cavities 33 and 33' in alignment, and the portions are then coupled. As shown in the figures, first portion 31 and second portion 32 can include corresponding protrusions 35 and receptacles 36 for aiding in alignment of the cavities. A preferred coupling method is ultrasonic welding which results in an airtight, hermetic seal around each of the corresponding cavities 33 and 33'; thus, the powder-filled cavities 33' in second portion 32 and the empty cavities 33 in first portion 31 combine to form a plurality of individual, hermetically sealed chambers. Preferably, the sealed chambers are cylindrically or conically shaped, allowing the powder to freely flow from the chamber when the seal is broken during the dispensing process.

To aid in the ultrasonic welding of the individual chambers, surrounding each cavity 33' in second portion 32 is a molded raised ring 37. During the welding process, ring 37 concentrates and directs the ultrasonic energy to itself, thereby rapidly initiating the preferential softening and melting of ring 37 to join the two portions 31 and 32 and hermetically seal each of the individual chambers. As earlier indicated, portions 31 and 32 are preferably formed from high impact polystyrene. The characteristics of this material provide a superior ultrasonic welding of the two portions.

As previously discussed, one of cavities 33' in second portion 32 may be sealed or otherwise blocked at each end, thus preventing this cavity 33' from being filled with a dry powder dose 34. This feature provide a means for preventing inadvertent "double-dosing" when dispenser 30 is first rotatably inserted into a dry powder inhaler 10. Without this feature, the user could inadvertently depress the movable portion 17 of cover 12, piercing the seal on a powder-filled chamber 22 and releasing some or all of a drug dose 23, during the insertion process. The dose 23 would then be lost, or the user would rotate the disc 11 to what was believed to be the initial dose and release a second dose which could then be inhaled along with the residual powder from the inadvertent dispensing. By including an unfilled cavity, the multiple-dose dispenser of the present invention overcomes this disadvantage.

Figure 3:
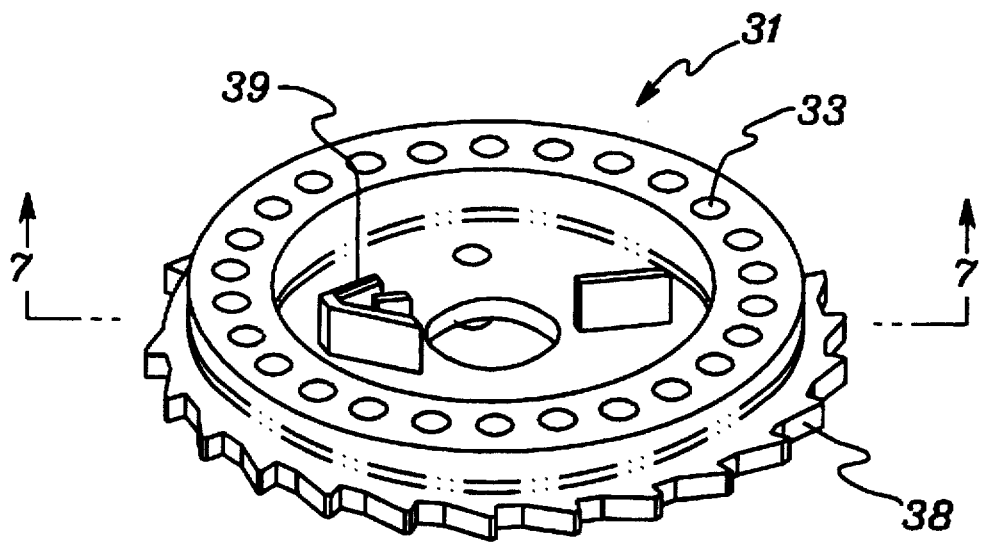
FIGS. 3 and 4 are perspective views of one embodiment of the first portion of the multiple-dose dispenser of the present invention.

Referring now to FIGS. 3 and 4, in one embodiment of the present invention, one of first portion 31 (shown) or second portion 32 may include a series of ratchet teeth 38 on its outer periphery, for functionally indexing the individual chambers into the proper dispensing position when dispenser 30 is in use with a dry powder inhaler 10. As illustrated, there is one ratchet tooth 38 corresponding to all but one sealed chamber, this being the chamber wherein the cavity in second portion 32 is sealed on each end, and therefore, the chamber does not contain a dose of powder. Thus, when the dose in the previous chamber has been administered, dispenser 30 will not rotate to the empty chamber.

Additionally, dispenser 30 may include means, such as tabs 39 on first portion 31, for facilitating insertion, removal and rotation of dispenser 30 with respect to inhaler 10. Dispenser 30 may include reference numerals or the like (not shown) corresponding to each of the sealed chambers, which are viewable through a window in inhaler 10 and which indicate how many doses remain in the dispenser.

This invention has been described in terms of specific embodiments, set forth in detail. It should be understood, however, that these embodiments are presented by way of illustration only, and that the invention is not necessarily limited thereto. Modifications and variations within the spirit and scope of the claims that follow will be readily apparent from this disclosure, as those skilled in the art will appreciate.

We claim:

1. A multiple-dose dispenser for use with dry powder inhalers, said multiple-dose dispenser comprising a first portion and a second portion, each portion having a plurality of cavities extending therethrough, wherein each of the cavities is closed on one end with a seal and wherein the first portion is bonded to the second portion such that each of the open cavities in the second portion is in alignment with one of the cavities in the first portion, thereby forming a plurality of sealed chambers.

2. The multiple-dose dispenser according to claim 1 wherein one of the cavities in the second portion is closed on each end.

3. The multiple-dose dispenser according to claim 1 wherein the first portion and the second portion are substantially disc-shaped and the plurality of cavities are circumferentially located.

4. The multiple-dose dispenser according to claim 3 wherein the first portion is mechanically bonded to the second portion by ultrasonic welding.

5. The multiple-dose dispenser according to claim 1 further comprising a drive means for functionally indexing the sealed chambers into a dispensing position in the dry powder inhaler.

6. The multiple-dose dispenser according to claim 5 wherein the drive means is a plurality of ratchet teeth on an outer periphery of the dispenser and wherein there is one less ratchet tooth than sealed chambers.

7. The multiple-dose dispenser according to claim 3 wherein the sealed chambers are substantially cylindrical or conical.

8. The multiple-dose dispenser according to claim 1 wherein the seal is a pierceable film of plastic, metal or laminate.

9. A method for producing a multiple-dose dispenser for use with a dry powder inhaler comprising the steps of:

providing a first portion and a second portion, each portion having a plurality of cavities extending therethrough;

blocking one end of each cavity with a seal;

filling each of the open cavities in the second portion with a unit dose of a dry powder;

bonding the first portion to the second portion such that the open end of each of the cavities in the second portion is aligned with an open end of one of the cavities in the first portion, forming a plurality of sealed chambers.

10. The method according to claim 9 wherein the step of filling each of the open cavities in the second portion comprises overfilling each cavity with an excess volume of a dry powder and removing the excess dry powder to form a level powder surface in each cavity.

11. The method according to claim 9 further comprising, after the step of blocking one end of each cavity with a seal, the step of blocking a second end of one of the cavities in the second portion with a seal.

12. The method according to claim 9 wherein the step of bonding the first portion to the second portion comprises ultrasonic welding wherein each of the sealed chambers is hermetically sealed.

* * * * *